(12) United States Patent
Olive et al.

(10) Patent No.: US 6,445,954 B1
(45) Date of Patent: Sep. 3, 2002

(54) PULSE GENERATOR HEADER LEAD INTRODUCER TOOL

(75) Inventors: Arthur L. Olive, Stacy; Ronald W. Heil, Jr., Roseville, both of MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 0 days.

(21) Appl. No.: 09/542,964

(22) Filed: Apr. 4, 2000

(51) Int. Cl.[7] .................................................. A61N 1/02
(52) U.S. Cl. ........................................................ 607/37
(58) Field of Search ................................... 607/122, 37

(56) References Cited

U.S. PATENT DOCUMENTS

| | | | | |
|---|---|---|---|---|
| 3,974,834 A | 8/1976 | Kane | .......................... | 128/418 |
| 4,046,151 A | 9/1977 | Rose | .......................... | 128/404 |
| 4,471,777 A | 9/1984 | McCorkle, Jr. | ......... | 128/303 R |
| 4,576,162 A | 3/1986 | McCorkle | .............. | 128/303 R |
| 4,582,056 A | 4/1986 | McCorkle, Jr. | ........ | 128/303 R |
| 4,998,975 A | 3/1991 | Cohen et al. | ........... | 128/419 D |
| 5,103,821 A | 4/1992 | King | .......................... | 128/419 P |
| 5,224,491 A | 7/1993 | Mehra | ....................... | 128/784 |
| 5,336,252 A | 8/1994 | Cohen | ....................... | 607/119 |
| 5,342,413 A | 8/1994 | Hirschberg et al. | ........ | 607/126 |
| 5,387,234 A | 2/1995 | Hirschberg | ................ | 607/129 |
| 5,409,469 A | 4/1995 | Schaerf | ..................... | 604/282 |
| 5,411,527 A | 5/1995 | Alt | ............................. | 607/5 |
| 5,423,806 A | 6/1995 | Dale et al. | .................... | 606/15 |
| 5,531,779 A | 7/1996 | Dahl et al. | .................. | 607/119 |
| 5,639,276 A | 6/1997 | Weinstock et al. | .......... | 606/129 |
| 5,649,974 A | 7/1997 | Nelson et al. | ............... | 607/122 |
| 5,674,217 A | 10/1997 | Wahlstrom et al. | ........... | 606/15 |
| 5,674,272 A | 10/1997 | Bush et al. | .................. | 607/122 |
| 5,713,867 A | 2/1998 | Morris | ........................ | 604/164 |
| 5,769,858 A | 6/1998 | Pearson et al. | ............. | 606/108 |
| 5,843,141 A | 12/1998 | Bischoff et al. | .............. | 607/37 |
| 5,851,226 A | 12/1998 | Skubitz et al. | .............. | 607/126 |
| 5,871,530 A | 2/1999 | Williams et al. | ............ | 607/122 |
| 5,897,584 A | 4/1999 | Herman | ...................... | 607/122 |
| 5,902,331 A | 5/1999 | Bonner et al. | .............. | 607/122 |
| 5,994,444 A | 11/1999 | Trescony et al. | ........... | 524/429 |
| 6,038,472 A | 3/2000 | Williams et al. | ................ | 607/5 |
| 6,043,273 A | 3/2000 | Duhaylongsod | ............ | 514/478 |

*Primary Examiner*—Scott M. Getzow
(74) *Attorney, Agent, or Firm*—Schwegman, Lundberg, Woessner & Kluth, P.A.

(57) ABSTRACT

A cardiac lead introducing apparatus, the cardiac lead introducing apparatus having a sleeve with a peripheral surface, a first end and a second end, where the sleeve includes an opening extending from the first end to the second end and adapted to hold at least a portion of a cardiac lead. The cardiac lead introducing apparatus further includes a first slit extending from the peripheral surface to the opening and from the first end to the second end which permits the sleeve to separate so the cardiac lead can pass through the cardiac lead introducing apparatus without any longitudinal motion of the device with respect to the cardiac lead. In one embodiment, the diameter of the opening is smaller than the outer diameter of the cardiac lead which permits the cardiac lead to be held static within the introducing apparatus as the lead connector of the cardiac lead is inserted into the socket of an implantable pulse generator connector block.

23 Claims, 12 Drawing Sheets

PULSE GENERATOR HEADER LEAD INTRODUCER TOOL

TECHNICAL FIELD

The present subject matter relates generally to implantable medical devices, and particularly, but not by way of limitation, to an apparatus and method for introducing a lead into a connector block of a pulse generator.

BACKGROUND

Implantable pulse generators are integrated, highly sophisticated systems comprising a lead and a pulse generator. The lead is the only link between the electronics in the pulse generator and the heart. Thus, the lead plays a critical role of delivering the output pulses from the pulse generator to the myocardium and transferring the intracardiac electrogram from the myocardium to the sensing circuits of the pulse generator.

The main components of the cardiac lead includes one or more electrodes, one or more lead conductors, lead insulation, and a lead connector. Generally, the one or more electrodes are each individually coupled to the one or more lead conductors, which in turn are coupled to the lead connector. The lead insulation electrically and physically isolates the lead conductors and provides a surface on which the one or more electrodes reside.

The lead conductor of the cardiac lead is typically a coil of wire that conducts electric current from the pulse generator to the electrode. The conductor is also responsible for conducting the sensed cardiac signals from the electrodes to the sensing amplifier of the pulse generator. One common conductor design is of a multifilar coil arrangement which is helically coiled to create an empty core. The empty core allows for the passage of a stainless steel stylet which aids in the implanting of the cardiac lead.

There are two basic approaches for the implantation of an implantable pulse generator. The first is the epicardial approach and the second is the transvenous approach. The epicardial approach calls for direct application of electrodes on the heart. The transvenous approach calls for inserting the cardiac lead into the patient's heart through the cardiac veins. Today, approximately 95% of all pacemaker implantations are performed transvenously.

Once the cardiac lead has been implanted into the patient's heart the lead connector is coupled to the pulse generator. Lead connectors typically have low-profile, in-line connector pins which are inserted into a socket located on the pulse generator. The lead connector also has sealing rings which prevent fluids from entering the socket of the pulse generator once the lead connector has been seated in the pulse generator. Once seated in the socket, the in-line connector pins make contact with terminals which couple the one or more electrodes on the surface of the cardiac lead with the electronics within the pulse generator.

Possible problems can arise when the lead connector is inserted into the socket of the implantable pulse generator. For example, it is possible to bend the cardiac lead at an acute angle as the lead connector is being inserted into the socket. When this occurs, there is the possibility of over-flexing the lead conductor within the cardiac lead causing the conductor to stress and/or break. A damaged lead conductor could then lead to intermittent sensing and/or pacing by the pulse generator, which in turn may endanger the patient's health. This problem is due, in part, to the flexibility of the lead and the seal drag created in the socket as the cardiac lead is inserted into the pulse generator with the required insertion force.

Recommendations for inserting lead connectors into a pulse generator include inserting the lead connector straight into the pulse generator, being careful to avoid bending or pinching the cardiac lead as it is being inserted into the socket of the pulse generator. Additionally, it is recommended to avoid tight bends in the lead terminal during the insertion procedure and when placing the pulse generator into the patient. Even with these recommendations, given the time critical nature of implanting a pulse generator there is still the danger of damaging the cardiac lead while it is being inserted into the pulse generator. Therefore, a need exists for reducing the danger of damaging the cardiac lead as it is being inserted into an implantable pulse generator.

SUMMARY

The present subject matter provides for a reduced likelihood of damage to a flexible lead as the lead is inserted into a device. In one embodiment, the present subject matter provides for an apparatus and method for supporting a cardiac lead as the lead is inserted into the implantable pulse generator. The apparatus and method of the present subject matter provide a sleeve, or collar, disposed at least partially around the body of the cardiac lead. The sleeve provides a surface with which to hold the cardiac lead and also provides support to the lead to prevent bending or pinching the cardiac lead as it is being inserted into the socket of the pulse generator.

In one embodiment, the apparatus comprises the sleeve. The sleeve is an elongate body having a peripheral surface, a first end and a second end. The sleeve also includes an opening extending from the first end to the second end, where the opening in the sleeve at least partially surrounds and supports (e.g., prevents lateral deflections of the lead) at least a portion of the cardiac lead. In one embodiment, the opening is eccentric or centric relative the longitudinal axis of the sleeve. The sleeve also includes a first slit extending from the peripheral surface to the opening and from the first end to the second end, where the cardiac lead is passed through the first slit to remove the sleeve from the cardiac lead.

Cardiac leads typically include a lead connector at the proximal end of the lead. When coupling the cardiac lead to the implantable pulse generator, the lead connector is inserted into the connector block of the implantable pulse generator. In one embodiment, the sleeve of the present subject matter is positioned distal to the lead connector to allow for the lead connector. In one embodiment, the sleeve is positioned on the lead so that the lead connector can be fully seated within the connector block while the sleeve provides support to the cardiac lead.

In an additional embodiment, the sleeve includes a releasable closure strip which joins the sleeve along the first slit. In one embodiment, when the releasable closure strip is removed, the sleeve self-opens (e.g., sleeve returns to a relaxed state) to form a pass through opening in the sleeve which allows the cardiac lead to pass through the pass through opening.

In an alternative embodiment, the sleeve includes a second slit extending from the peripheral surface to the opening and from the first end to the second end. Having a first and second slit divides the sleeve into a first and second housing portion. A hinge is provided along the second slit to join the first and second housing portions and provides a point around which the two housing portions pivot once the releasable strip is removed from the first slit.

DETAILED DESCRIPTION

In the following detailed description, reference is made to the accompanying drawings which form a part hereof and in which is shown by way of illustration specific embodiments in which the invention may be practiced. These embodiments are described in sufficient detail to enable those skilled in the art to practice and use the invention, and it is to be understood that other embodiments may be utilized and that logical, and structural changes may be made without departing from the spirit and scope of the present invention. The following detailed description is, therefore, not to be taken in a limiting sense and the scope of the present invention is defined by the appended claims and their equivalents.

Figure 1:
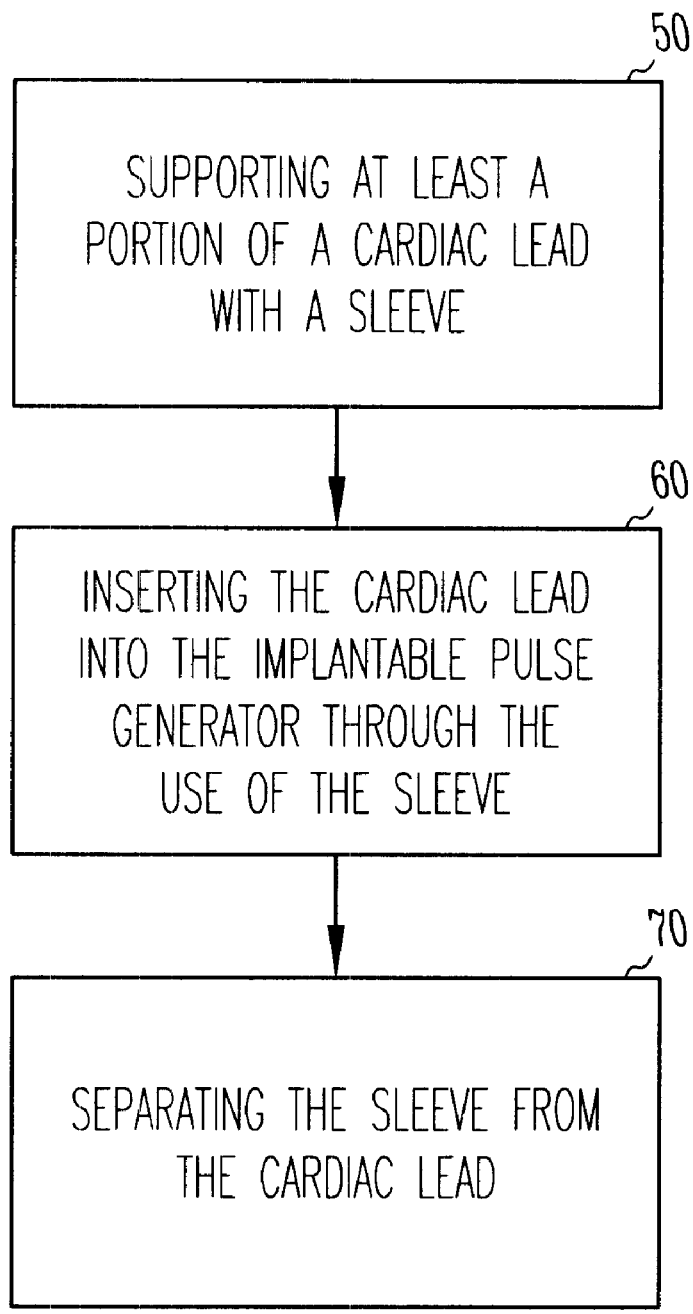
FIG. 1 is one embodiment of a method according to the present subject matter.

Referring now to FIG. 1, there is shown one embodiment of a method according to the present subject matter. In one embodiment, the method of the present subject matter is designed to provide support for a lead body of a cardiac lead as the cardiac lead is inserted into an implantable medical device. As will be discussed, inserting a cardiac lead into an implantable medical device, such as an implantable pulse generator, can cause damage to the cardiac lead (e.g., fracturing and/or breaking conductor wires within the lead body) if the lead body is bent or kinked as the connector portion of the lead is inserted into the medical device.

As pointed out above, the cardiac lead is the critical link between the pulse generator and the patient. In particular, the placement of the lead electrode(s) in or on the patient's heart is critical. Once positioned, it is highly desirable to have the electrode(s) remain in position. Immediately after the initial placement of the lead electrode(s) and prior to the onset of significant wound healing and fibrosis, the lead is not connected to the pulse generator. The process of making this necessary connection to the pulse generator can easy, but also can be quite difficult. During those instances when the connection process is difficult, the lead electrode(s) may be accidentally pulled away from the physician-selected site of placement. Such an accidental dislodgement is usually not catastrophic, but does require additional time and effort to reposition the electrode(s) prior to another attempt to connect the lead to the pulse generator. The present subject matter aids in inserting the proximal end of the lead into the pulse generator while simultaneously preventing the distal lead electrode(s) from being disengaged from the heart tissue.

For the present subject matter, at least a portion of a cardiac lead is supported with a sleeve, 50. In addition to supporting the cardiac lead, the sleeve also provides for a surface with which to grip and handle (i.e., control) the cardiac lead. In one embodiment, the sleeve is positioned at a point that is distal to the lead connector of the cardiac lead. Additionally, the sleeve is adapted to either completely encircle or to at least partially encircle the body of the cardiac lead, as will be described later. Through the use of the sleeve, the cardiac lead is inserted into the implantable pulse generator, 60. In one embodiment, the sleeve is positioned on the cardiac lead at a predetermined location distal the lead connector such that the sleeve abuts the connector block of the implantable medical device when the lead connector is seated in the connector block. At 70, once the cardiac lead is inserted into the pulse generator, the sleeve is then separated from the cardiac lead. In one embodiment, a slit is provided in the sleeve, where in separating the sleeve from the cardiac lead, the slit is opened to a size which permits the cardiac lead to pass through the slit and release the sleeve from the cardiac lead.

Figure 2:
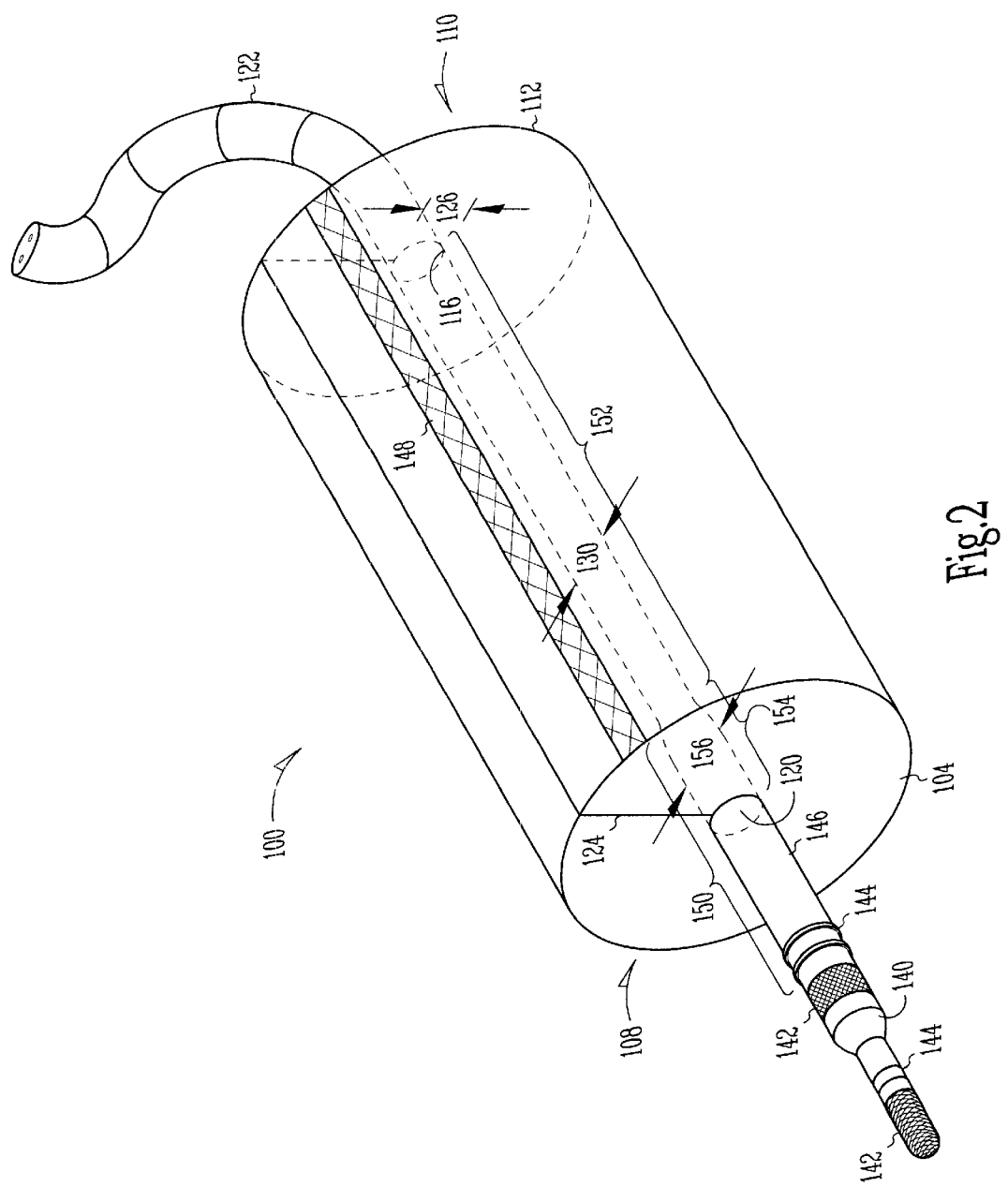
FIG. 2 is a schematic view of one embodiment of an apparatus according to the present subject matter.

Referring now to FIG. 2, there is shown one embodiment of an apparatus 100 according to the present subject matter. In one embodiment, the apparatus 100 is designed to be used as a cardiac lead introducing apparatus. The apparatus 100 includes a sleeve 104 which has a first end 108 and a second end 110. The apparatus 100 further includes a peripheral surface 112 and an interior surface 116. In one embodiment, the interior surface 116 defines an opening 120 which extends from the first end 108 to the second end 110. In one embodiment, the opening 120 is adapted to hold at least a portion of a cardiac lead 122. The sleeve 104 further includes a first slit 124 extending from the peripheral surface 112 to the opening 120 and from the first end 108 to the second end 110.

In one embodiment, the cardiac lead introducing apparatus of the present subject matter is adapted to securely hold at least a portion of a cardiac lead (e.g., cardiac lead 122), as are known. In one embodiment, the apparatus 100 holds the cardiac lead through an interference fit (a friction fit) between the interior surface 116 of the apparatus 100 and at least a portion of the body of the cardiac lead. One manner of holding the cardiac lead body with the apparatus 100 is where a first diameter 126 of the opening 120 is smaller than an outer diameter 130 of the body of the cardiac lead 122. In one embodiment, the first diameter 126 of the opening 120 is approximately five (5) percent smaller than the outer diameter 130 of the body of the cardiac lead 122. Alternatively, other values for how much smaller the first diameter 126 of the opening 120 is with respect to the outer diameter 130 of the body of the cardiac lead 122 can be used, as long as the compressive force transferred at the interior surface 116 to the body of the cardiac lead is sufficient to prevent the cardiac lead body from sliding, or moving, in the opening 120 of the apparatus 100. Alternatively, the force (causing grasping) exerted on the cardiac lead through the interference fit (i.e., by the friction fit) between the interior surface 116 of the apparatus 100 and the body of the cardiac lead must be greater than the insertion force of the cardiac lead (causing drag) into the connector block of the pulse generator by at least fifty percent (50%).

In the present embodiment, the apparatus 100 is positioned around the body of the cardiac lead 122 near or on at least a portion of the lead connector 140. In one embodiment, the sleeve 104 is shown distal at least a portion of the lead connector 140. As FIG. 2 shows, the lead connector 140 includes terminal rings 142, lead sealing ring zones 144 and a lead connector body 146, as are known. When coupled to the cardiac lead 122, the apparatus 100 provides a large surface area, with respect to the body of the cardiac lead 122, with which to grip and handle the lead connector 140 portion of the cardiac lead 122. Furthermore, the apparatus 100 provides support to the cardiac lead body as the lead connector 140 is inserted into the connector block of an implantable pulse generator. The additional support provided by the apparatus 100 helps to prevent the cardiac lead 122 from being bent as it is inserted into the connector block. Additionally, in one embodiment, the apparatus 100 is positioned along the body of the cardiac lead so that the first end 108 of the apparatus 100 abuts the connector block when the lead connector 140 has been fully seated in the connector block of the pulse generator. In one embodiment, this latter feature of apparatus 100 is applicable to the embodiments disclosed herein.

In a further embodiment, the apparatus 100 further includes a key indicator 148 which is used to align the lead connector 140 in a proper rotation relative the connector block of the implantable pulse generator. In one embodiment, the key indicator 148 is a portion of the sleeve having a contrasting color or texture relative the remainder of the sleeve 104. Alternatively, the slit 124 can function as a key indicator to help align the lead connector 140 with the connector block.

In one embodiment, once the lead connector 140 is seated in the connector block, the apparatus 100 is removed from around the body of the cardiac lead 122 by passing the body of the cardiac lead 122 through the first slit 124 in the apparatus 100. Thus, the device is removed from the body of the cardiac lead without requiring access to either end of the cardiac lead. In one embodiment, the apparatus 100 is constructed of a flexible material which allows the distance between the walls created by the first slit 124 to become larger (i.e., to separate) as the body of the cardiac lead 122 to pass through the first slit 124.

In one embodiment, the material is a medical grade polymer, copolymers and/or polymer blends (e.g., biocompatible medical grade polymer, copolymers and/or polymer blends) such as polypropylene. Other biocompatable materials, such as the various polyethylenes, polyurethanes or silicone rubbers may also be used. Additionally, the sleeve has a length between the first end 108 and the second end 110 which is adapted to adequately support the body of the cardiac lead 122 as the lead connector 140 is inserted into the connector block. In one embodiment, the length of the sleeve is from seven and one-half (7.5) centimeters to ten and one-half (10.5) centimeters. Additionally, the sleeve has a diameter in the range of six (6) millimeters to twenty-four (24) millimeters.

In an additional embodiment, the cardiac lead 122 includes a strain relief boot 150. In one embodiment, the strain relief boot 150 forms a portion of the lead connector body 146. In one embodiment, the strain relief boot 150 has an outer diameter which is larger than the outer diameter 130 of the body of the cardiac lead 122. In one embodiment, to accommodate the strain relief boot 150, the opening 120 includes a first region 152 having the first diameter and a second region 154 having a second diameter 156, where the first diameter is less than the second diameter, where the first region 152 is adapted to hold at least a portion the cardiac lead body 122 and the second region 154 is adapted to hold at least a portion of the strain relief boot 150.

Figure 3:
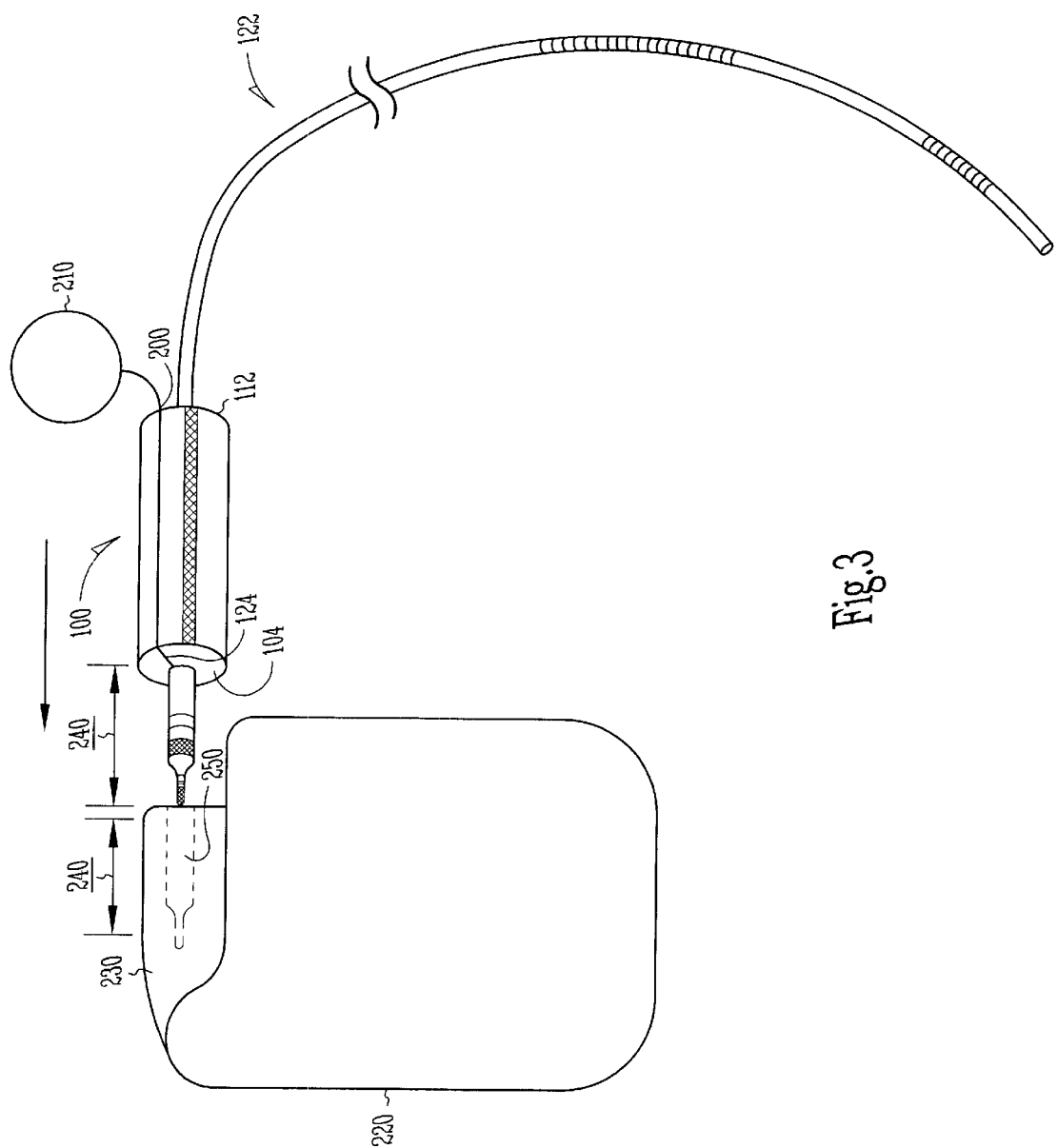
FIG. 3 is a schematic view of one embodiment of an apparatus and an implantable pulse generator according to the present subject matter.

Referring now to FIG. 3, there is shown one embodiment of the apparatus 100 positioned around at least a portion of the body of the cardiac lead 122. The apparatus 100 is shown to include a releasable closure strip 200. In one embodiment, the releasable closure strip 200 joins the sleeve 104 along the first slit 124, where the releasable closure strip 200 extends longitudinally between the first end 108 and the second end 110 of the sleeve 104. In one embodiment, the closure strip 200 is coupled to the sleeve and bridges the first slit 124. In an additional embodiment, the closure strip 200 is constructed of the same material as the sleeve 104. In an alternative embodiment, the closure strip 200 is constructed of a material that is harder (e.g., higher modulus) than the material of the sleeve 104.

When the closure strip 200 is pulled with sufficient force, the material of the sleeve approximately surrounding the closure strip 200 tears. In one embodiment, the material of the sleeve approximately surrounding the closure strip 200 is weakened so as to allow the closure strip 200 to more easily tear the material of the sleeve 104. In one embodiment, weakening the material of the sleeve 104 includes having perforations through the sleeve 104 material along the length of the first slit 124. In an alternative embodiment, weakening the material of the sleeve 104 includes reducing the thickness of the sleeve 104 material adjacent the closure strip 200 so as to allow the closure strip 200 to more easily tear the material of the sleeve 104. Once torn, the cardiac lead 122 can be passed through the first slit 124 as previously described. Alternatively, once the closure strip 200 has been removed the sleeve 104 can be opened about a hinge to allow the cardiac lead 122 to be released from the apparatus 100. To aid in pulling the closure strip 200, the releasable closure strip 200 can further include a ring 210 which is attached to one end of the releasable closure strip 200.

FIG. 3 also shows one embodiment of an implantable pulse generator 220. In one embodiment, the lead connector body of catheter 122 is inserted into a lead connector block 230 (also referred to as a "header") of the implantable pulse generator, where the apparatus 100 provides support to the body of the cardiac lead 122. In one embodiment, the implantable pulse generator 220 is a pacemaker, as is known. In an additional embodiment, the implantable pulse generator 220 is an implantable cardioverter-defibrillator, as is known. Alternatively, the implantable pulse generator 220 is any device which receives a catheter.

Typically, inserting, or coupling, the cardiac lead 122 to the implantable pulse generator 220 involves gripping the body of the cardiac lead near, or at, the lead connector body 146. The lead connector body 146 is then inserted into an opening in the lead connector block 230. As the cardiac lead is being inserted into the connector block 230 there is a possibility the body of the cardiac lead can be bent or flexed at, or around, the area where the lead is being held. If the body of the lead is flexed or bent too much damage can occur to the lead. Examples of damage include, but are not limited to, stressing or fracturing one or more conductor wires within the lead body. This can occur when the lead body is bent at an acute angle relative the position of the lead connector located within connector block 230. Once the lead is damaged a replacement lead is needed. Replacing the damaged lead, therefore, costs both money to replace the lead and time to remove and replace the damaged lead.

In one embodiment, apparatus 100 of the present subject matter provides support to a region of the cardiac lead that is being held as the lead is inserted into the connector block 230. In one embodiment, when a cardiac lead is to be coupled to an implantable pulse generator, the apparatus 100 is gripped, the lead connector body and the opening in the connector block are aligned, and pressure is applied through the apparatus 100 to insert the to the lead connector body into the connector block. Additionally, the apparatus 100 provides a large surface area with which to grip and control the cardiac lead. In an additional embodiment, the first end 108 of the sleeve 104 is positioned along the body of the catheter lead 122 so that the first end 108 abuts the connector block 230 when the lead connector body is fully seated in the connector block 230. In one embodiment, this aspect of the present subject matter is shown in FIG. 3, where the distance between the proximal end of the cardiac lead and the first end 108 of the sleeve 104, as shown by 240, is approximately equal to the length, shown by 240, of a catheter socket 250 in the connector block 230.

Figure 4:
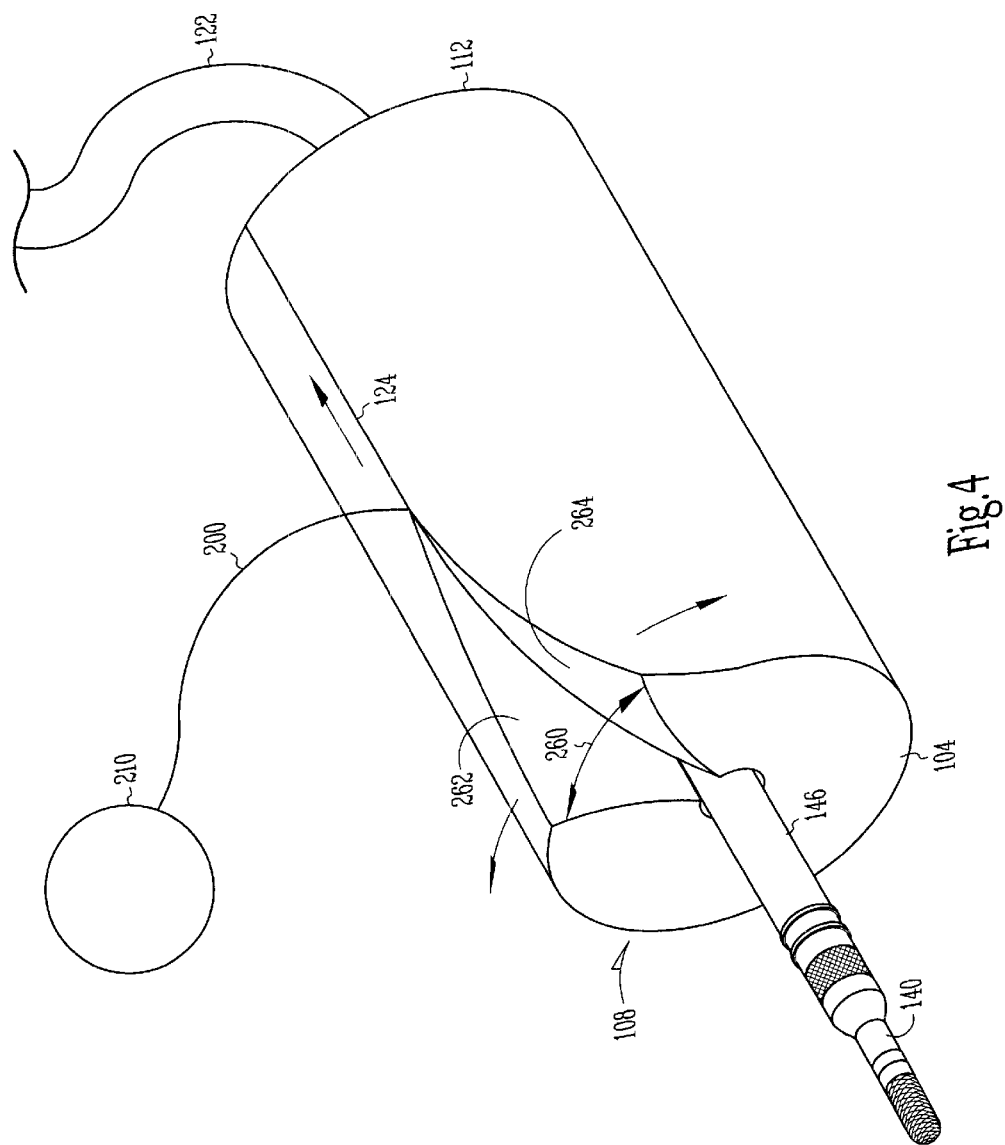
FIG. 4 is a schematic view of one embodiment of an apparatus according to the present subject matter.

Referring now to FIG. 4, there is shown an additional embodiment of the apparatus 100 according to the present subject matter. In one embodiment, the slit 124 of the sleeve 104 is adapted to be self-opening to create a pass through opening 260 in the sleeve 104. In one embodiment, the pass through opening 260 is defined by a first surface 262 and a second surface 264 of the sleeve 104. In one embodiment, the opening 260 is kept closed by the releasable closure strip 200, where as the releasable closure strip 200 is removed from the sleeve 104 the first and second surfaces 262 and 264 separate (as shown by the arrow in FIG. 4) to create the pass through opening 260. In an alternative embodiment, the opening 260 is kept closed by a releasable closure strip in the form of a clip as will be described in detail later in this document.

In one embodiment, the energy to cause the sleeve 104 to self-open, creating the pass through opening 260, is stored in the body of the sleeve 104 (potential energy store when sleeve 104 is held closed, and released when the strip 200 removed). The releasable closure strip 200 holds the first and second surfaces 262 and 264 adjacent each other to form the first slit 124. As the releasable closure strip 200 is removed, the energy stored in the body of the sleeve 104 is released to cause the first and second surfaces 262 and 264 separate. FIG. 4 shows one embodiment of the releasable closure strip 200 being removed from the sleeve 104, where the pass through opening 260 is formed as the sleeve 104 peels open.

Figure 5:
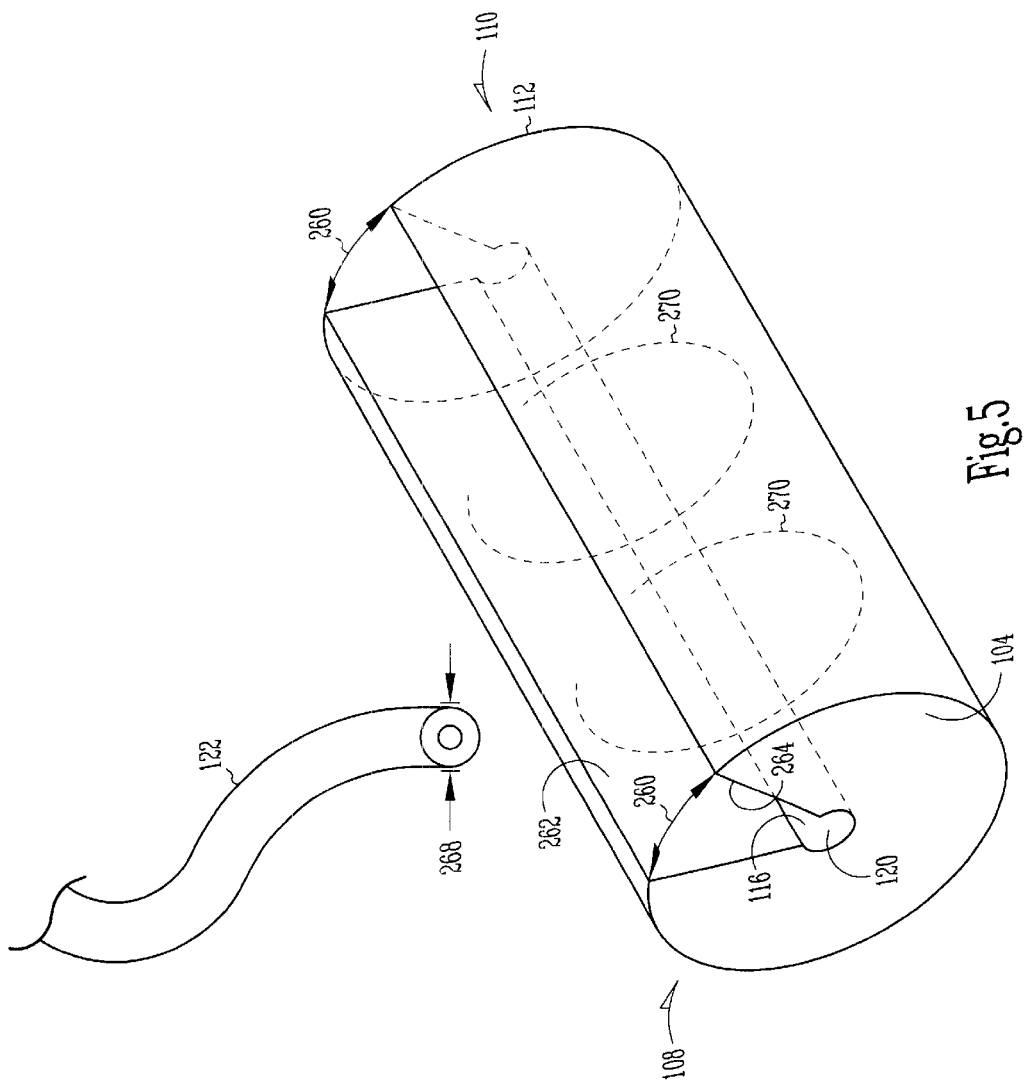
FIG. 5 is a schematic view of one embodiment of an apparatus according to the present subject matter.

Referring now to FIG. 5, there is shown one embodiment of the sleeve 104 according to the present subject matter. In the present embodiment, the sleeve 104 is shown where the material of the sleeve 104 is in a relaxed state. As previously discussed, when the material of the sleeve 104 is in the relaxed state the pass through opening 260 is present. As shown in FIG. 5, the pass through opening 260 extends from the first end 108 to the second end 110 of the sleeve 104. When the sleeve 104 has been opened (i.e., the pass through opening 260 is present) the opening 120 defined by the interior surface 116 expands out to join with the pass through opening 260.

In one embodiment, in the relaxed state the area in which the opening 120 expands out to join the pass through opening 260 has a width 268 which is greater than or equal to any diameter measurement of the body of the cardiac lead 122. This allows the cardiac lead 122 to pass through the opening 120 into the pass through opening 260 without having to cause deformation of either the body of the lead 122 or the sleeve 104. However, when the pass through opening 260 is not present (i.e., the closure strip 200 has not been removed) the interior surface 116 of the opening 120 holds the body of the cardiac lead 122, as previously discussed.

FIG. 5 also provides an additional embodiment of the self-expanding sleeve 104 structure. The sleeve 104 shown in FIG. 5 shows one or more expansion ribs 270 associated with the sleeve 104. In one embodiment, the expansion ribs 270 are positioned in, or on, the body of the sleeve 104 and serve to provide additional force to open the sleeve 104. In one embodiment, the expansion ribs 270 are constructed of either a metal or a polymer, where polymer expansion ribs have less flexibility (greater rigidity) than the polymer used to create the sleeve 104. In an additional embodiment, one expansion rib extending the length of the sleeve 104 is provided either in or on the sleeve 104.

Figure 6:
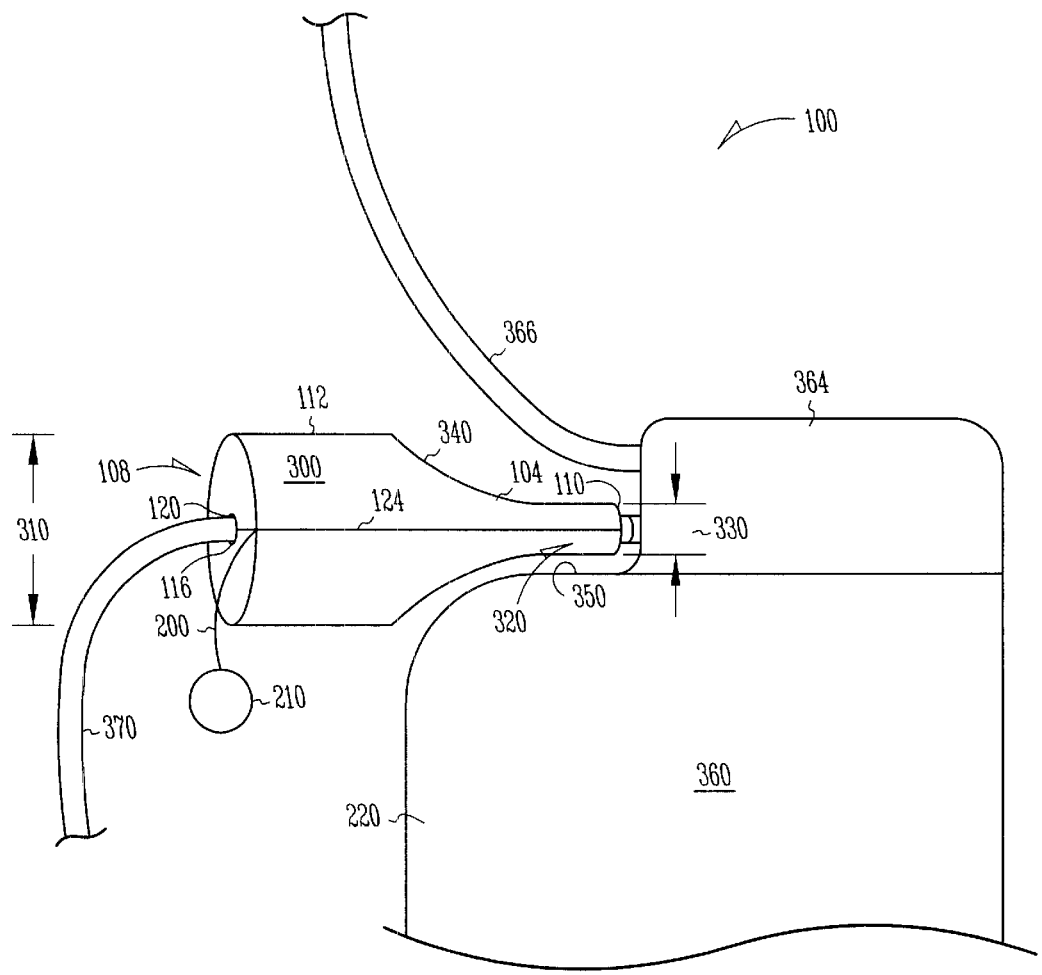
FIG. 6 is a schematic view of one embodiment of an apparatus and an implantable pulse generator according to the present subject matter.

Referring now to FIG. 6, there is shown an additional embodiment of an apparatus 100 according to the present subject matter. The apparatus 100 includes the sleeve 104 having a first end 108 and a second end 110. The sleeve 104 also includes the inner surface 116 and the opening 120 that extends along a longitudinal axis of the sleeve, as previously described. The sleeve 104 further includes the peripheral surface 112, where in the present embodiment the peripheral surface 112 defines a first region 300 having a first outer diameter 310 at the first end 108 of the sleeve 104. The peripheral surface 112 also defines a second region 320 having a second outer diameter 330 at the second end 112 of the sleeve 104. In one embodiment, the first outer diameter 310 is greater than the second outer diameter 330, where the peripheral surface 112 defines a tapered region 340 that joins the first region 300 and the second region 320 of the sleeve 104.

In one embodiment, the apparatus 100 is provided with the second region 320 of the sleeve 104 (i.e., a region having a smaller cross-sectional area relative the remaining portion of the sleeve) to allow for use of the sleeve 104 in inserting catheter lead into connector blocks that have relatively small clearance between the upper portion of the implantable pulse generator and the opening of the catheter lead socket. FIG. 6 provides one example of the use of apparatus 100, where the sleeve 104 has the tapered region 340 from the first region 300 to the second region 320 which allows the second region 320 to support the catheter lead while the second region 320 can pass over the upper portion 350 of the implantable pulse generator 360. In addition, when the connector block 364 includes two or more catheter lead sockets, the second region 320 of the sleeve 104 allows for the catheter lead to be supported while the sleeve 104 passes between the upper portion 350 of the implantable pulse generator 360 and a catheter lead 366 (a second catheter lead) which is positioned in connector block 364.

The embodiment of sleeve 104 shown in FIG. 6 is also shown having the releasable closure strip 200, where the releasable closure strip 200 joins the sleeve 104 along the first slit 124 and extends longitudinally between the first end 108 and the second end 110 of the sleeve 104. Once the releasable closure strip 200 is removed, the cardiac lead 370 is passed through the first slit 124, as previously described. Alternatively, once the closure strip 200 has been removed the sleeve 104 can be opened about a hinge to allow the cardiac lead to be released from the apparatus 100. To aid in pulling the closure strip 200, the releasable closure strip 200 can further includes ring 210 which is attached to one end of the releasable closure strip 200. In an alternative embodiment, ring 210 is replaced with a structure which allows for a person handling the apparatus 100 to pull the releasable closure strip 200. For example, the releasable closure strip 200 could include a tab having increased surface area on which to grip the end portion of the releasable closure strip 200.

Figure 7:
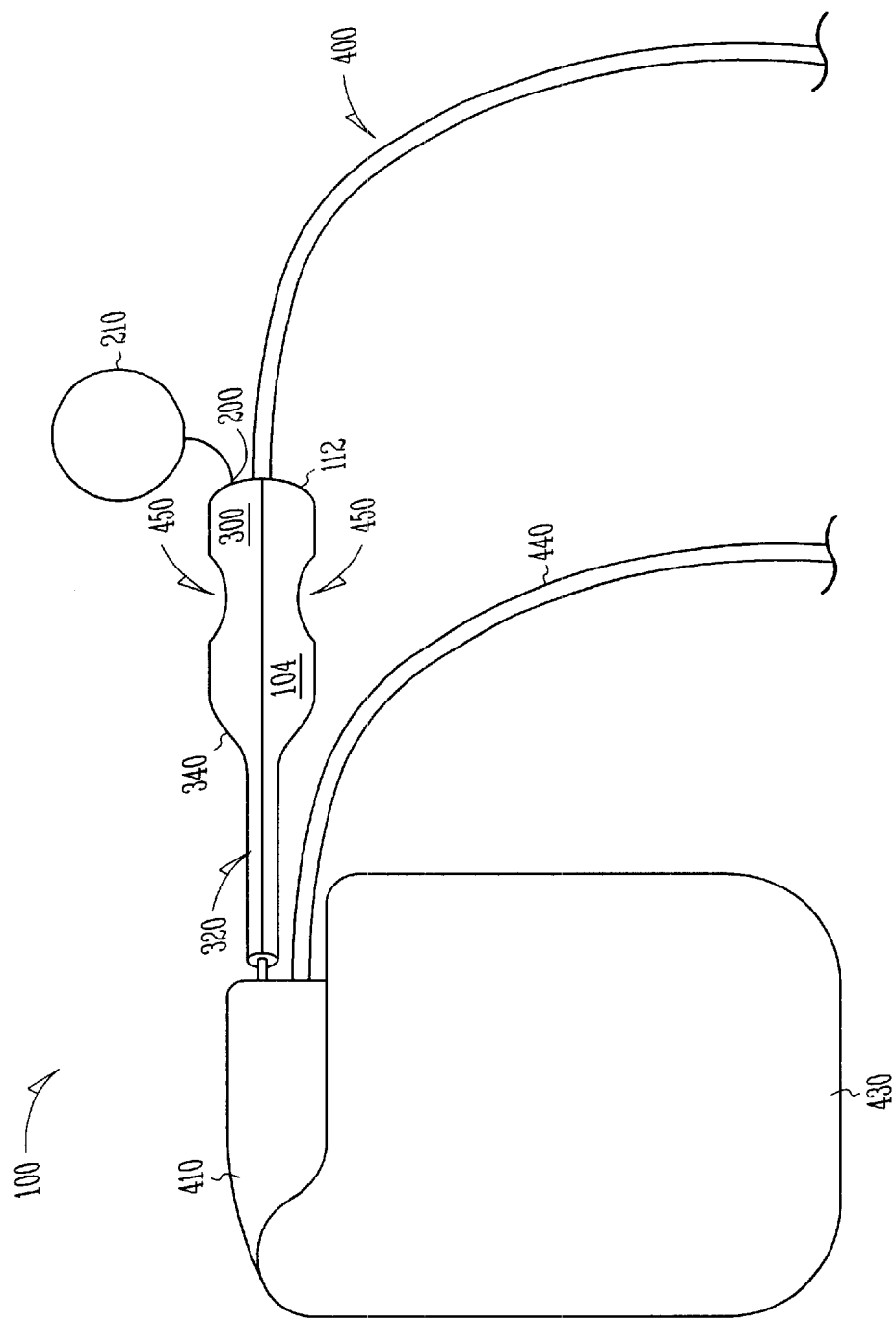
FIG. 7 is a schematic view of one embodiment of an apparatus and an implantable pulse generator according to the present subject matter.

Referring now to FIG. 7, there is shown an additional embodiment of the apparatus 100 according to the present subject matter. The apparatus 100 includes the sleeve 104, including the peripheral surface 112 which defines the first region 300, the tapered region 340 and the second region 320, as previously described. As shown in FIG. 7, the apparatus 100 is being used to assist in inserting a catheter lead 400 into a connector block 410, where the second region 320 is positioned above a second catheter lead 440 already coupled to the connector block 410. Additionally, the peripheral surface 112 in the first region 300 further defines recessed portions 450 of the sleeve 104 that conform to portions of a hand. In one embodiment, the recessed portions 450 are structured to conform to the shape of any combination of a thumb and one or more fingers of the hand.

Figure 8:
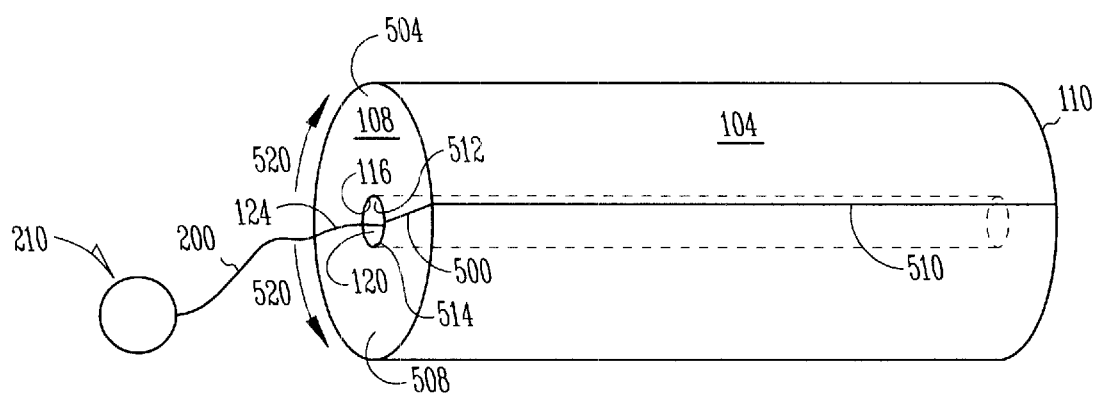
FIG. 8 is a schematic view of one embodiment of an apparatus according to the present subject matter.

Referring now to FIG. 8, there is shown an additional embodiment of the apparatus 100 according to the present subject matter. The apparatus 100 includes the sleeve 104 having the first end 108, the second end 110. The sleeve 104 also includes the opening 120 that extends along a longitudinal axis of the sleeve, as previously described. The sleeve 104 includes the peripheral surface 112, a first slit 124, and a second slit 500. In one embodiment, the second slit 500 extends from the peripheral surface 112 to the opening 120 and from the first end 108 to the second end 110.

When the first slit 124 and the second slit 500 are included, the sleeve 104 presents a first housing portion 504 and a second housing portion 508 which are joined, or coupled to each other, by the releasable closure strip 200 and a hinge 510, where the hinge 510 allows the first housing portion 504 to move relative the second housing portion 508. In one embodiment, the first housing portion 504 has a first inner surface 512 and the second housing portion 508 has a first inner surface 514, where the first inner surface 512 of the first housing portion 504 and the second housing portion 508 define the tubular opening 120 which extends from the first end 108 to the second end 110 of the first housing portion 504 and the second housing portion 508. In one embodiment, the opening 120 is as previously described. Additionally, the tubular opening 120 is adapted to releasably hold a cardiac lead body, as previously described.

In one embodiment, the hinge 510 extends longitudinally along the sleeve 104 at the second slit 500, joining the first housing portion 504 and the second housing portion 508 of the sleeve 104. In one embodiment, the sleeve 104 to moves about the hinge 510 (i.e., pivots about the hinge 510), as shown by the arrows at 520, to permit the first housing portion 504 and the second housing portion 508 to separate along the first slit 124. In one embodiment, the first housing portion 504 and the second housing portion 508 are separated to form an opening having an angle of between 90 to 180 degrees as defined by the walls of the first housing portion 504 and the second housing portion 508.

In one embodiment, the hinge 510 is formed from a portion of the sleeve 104 which bridges over the second slit 500 to couple the first housing portion 504 to the second housing portion 508. Alternatively, the hinge 510 is constructed from an additional strip of material which secures the first housing portion 504 to the second housing portion 508. In one embodiment, the additional strip of material is a biocompatible, medical grade polymer and/or co-polymer, such as polypropylene, polyethylene, polyurethane, or silicone for example. The hinge 510 is further adapted to be repeatedly opened and closed at least ten (10) times. In one embodiment, the ability to repeatably open and close the first housing portion 504 and the second housing portion 508 is important in allowing the apparatus 100 to be reattached to a catheter so that the lead connector can be removed from the connector block and/or reinserted into the connector block.

The embodiment of sleeve 104 shown in FIG. 8 is also shown having the releasable closure strip 200, where the releasable closure strip 200 joins the sleeve 104 along the first slit 124 and extends longitudinally between the first end 108 and the second end 110 of the sleeve 104, as previously described. Once the closure strip 200 has been removed the sleeve 104 can be opened about the hinge 510 to allow the cardiac lead to be released from the apparatus 100. To aid in pulling the closure strip 200, the releasable closure strip 200 further includes ring 210 which is attached to one end of the releasable closure strip 200. In an alternative embodiment, ring 210 is replaced with a structure which allows for a person handling the apparatus 100 to pull the releasable closure strip 200. For example, the releasable closure strip 200 could include a tab having increased surface area on which to grip the end portion of the releasable closure strip 200.

Figure 9:
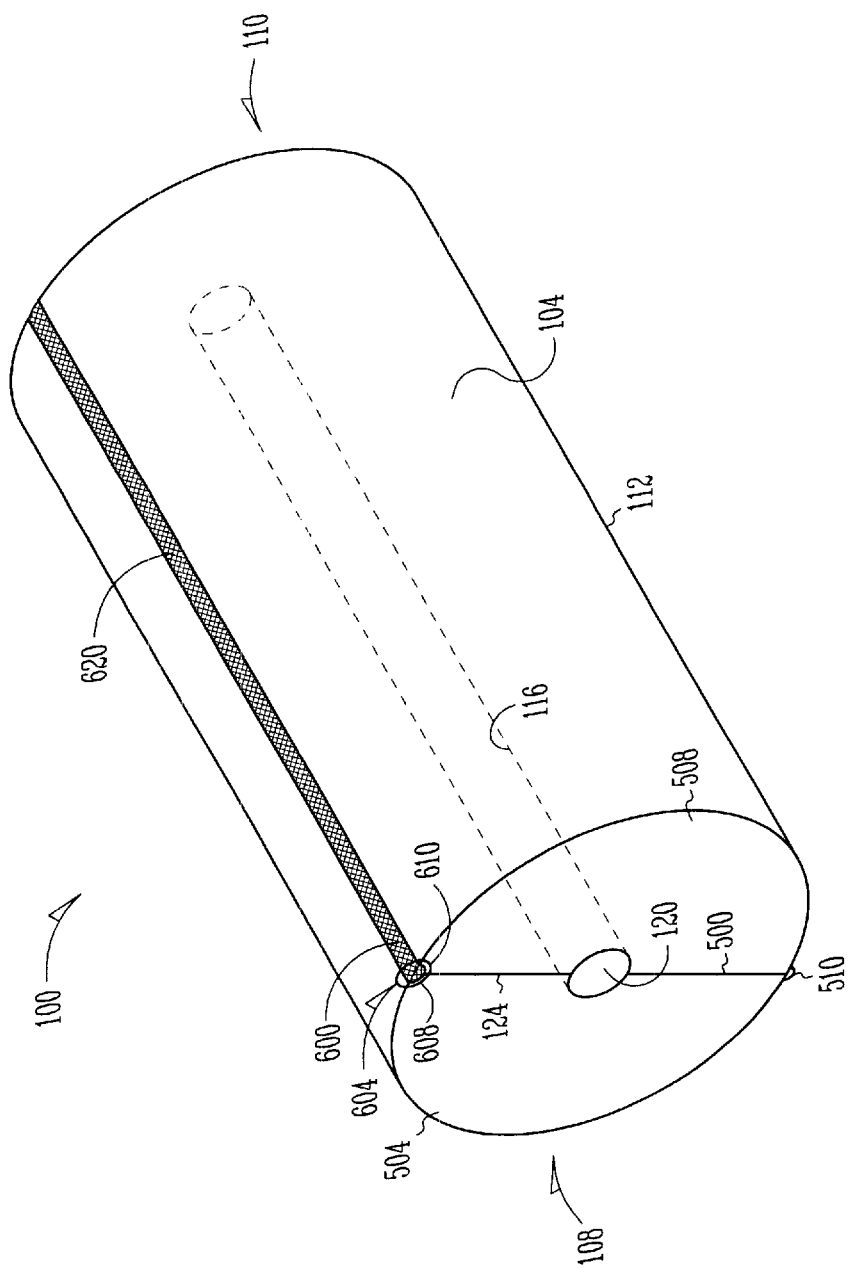
FIG. 9 is a schematic view of one embodiment of an apparatus according to the present subject matter.

Referring now to FIG. 9, there is shown an additional embodiment of the apparatus 100 according to the present subject matter. The apparatus 100 includes the sleeve 104 having the first end 108, the second end 110. The sleeve 104 also includes the inner surface 116 and the opening 120 that extends along a longitudinal axis of the sleeve, as previously described. The sleeve 104 further includes the peripheral surface 112, a first slit 124, and a second slit 500. In one embodiment, the second slit 500 extends from the peripheral surface 112 to the opening 120 and from the first end 108 to the second end 110.

When the first slit 124 and the second slit 500 are included, the sleeve 104 presents the first housing portion 504 and the second housing portion 508 which are joined, or coupled to each other, by a releasable closure strip 600 and the hinge 510. In one embodiment, the hinge 510 extends longitudinally along the sleeve 104 at the second slit 500, joining the first housing portion 504 and the second housing portion 508 of the sleeve 104. In one embodiment, the sleeve 104 to moves about the hinge 510, as previously described.

In one embodiment, the releasable closure strip 600 is a clip 604 which includes a first hook 608 and a second hook 610. In one embodiment, the first hook 608 forms a portion of the first housing portion 504 and the second hook 610 forms a portion of the second housing portion 508. The two halves of the clip 604 engage and can be disengaged by deforming the body of the sleeve 104 along the interface between the first housing portion 504 and the second housing portion 508 to allow the second hook 610 portion to engage, or disengage, the first hook portion 608 of the clip 604. Additionally, an extension portion 620 extends from the peripheral surface of the second housing portion 508 to provide a structure to facilitate hooking and unhooking the clip 604. For example, the extension portion 620 can be used to toggle the second hook 610 so as to allow the second hook 610 to engage the first hook 608 of the clip 604.

Additionally, in the embodiment shown in FIG. 8, the clip 604 extends along the entire longitudinal axis of the sleeve 104. Alternatively, the clip 604 extends along only a portion of the sleeve 104.

Figure 10:
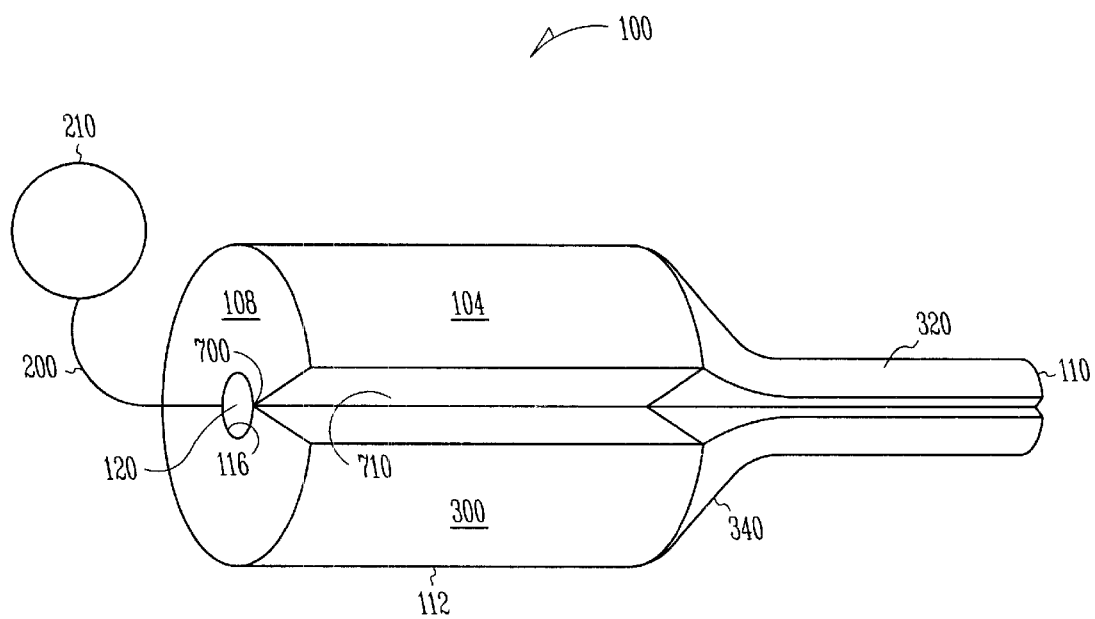
FIG. 10 is a schematic view of one embodiment of an apparatus according to the present subject matter.

Referring now to FIG. 10, there is shown an additional embodiment of the apparatus 100 according to the present subject matter. The apparatus 100 includes the sleeve 104 having the first end 108, the second end 110. The sleeve 104 also includes the inner surface 116 and the opening 120 that extends along a longitudinal axis of the sleeve, as previously described. The sleeve 104 further includes the peripheral surface 112, where in the present embodiment the peripheral surface 112 defines the first region 300, the tapered region 340, and the second region 320, as previously described. The apparatus 100 includes a hinge 700 which is adjacent the opening 120. In one embodiment, the hinge 700 is formed from the body of the sleeve 104. In an additional embodiment, the peripheral surface 112 further defines a region 710 into which the sleeve 104 moves as the sleeve 104 is moved about the hinge 700. In one embodiment, the region 710 extends along the longitudinal axis of the sleeve 104.

Figure 11:
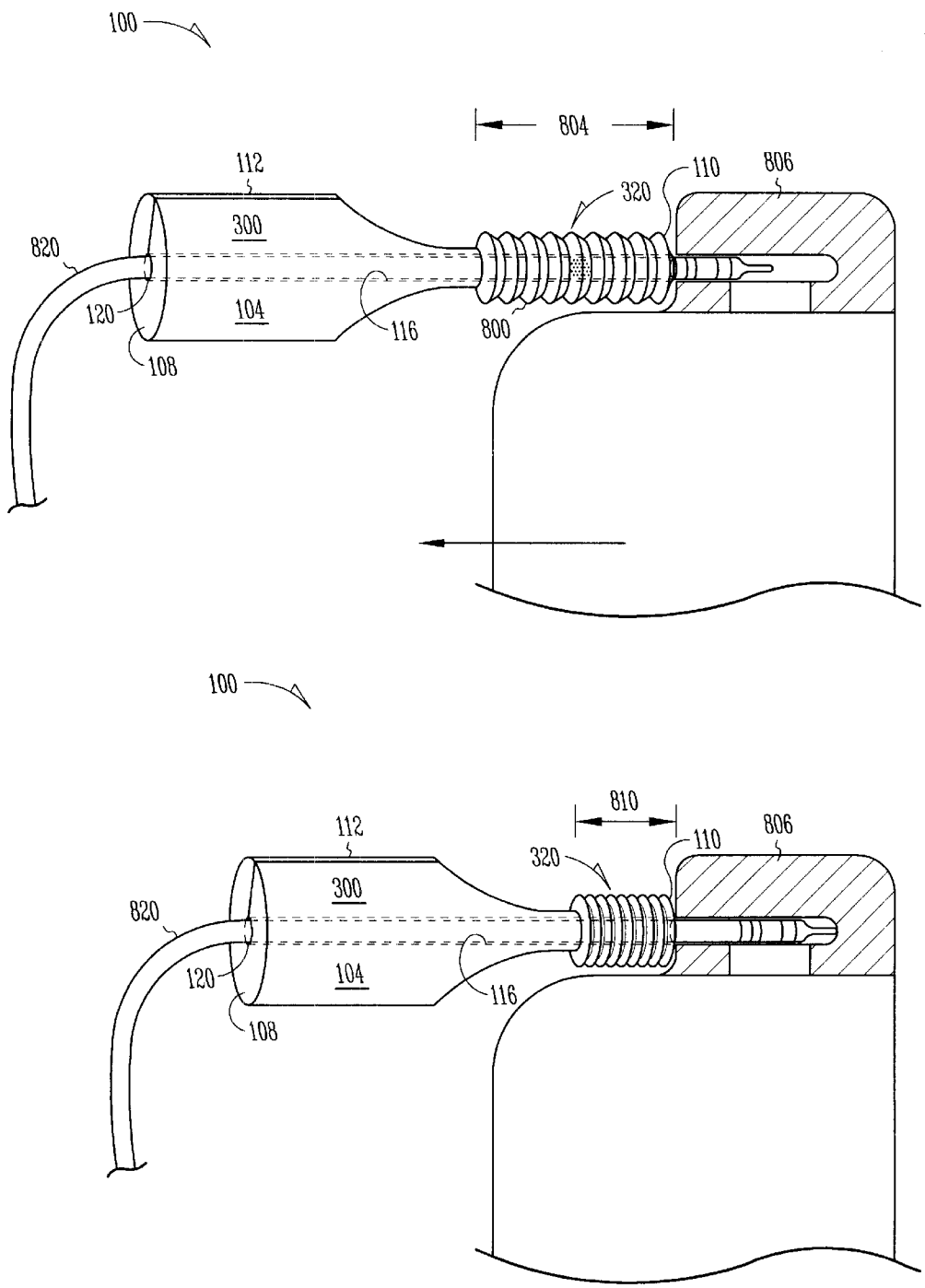
FIG. 11 is a schematic view of one embodiment of an apparatus and an implantable pulse generator according to the present subject matter.

Referring now to FIG. 11, there is shown an additional embodiment of an apparatus 100 according to the present subject matter. The apparatus 100 includes the sleeve 104 having a first end 108 and a second end 110. The sleeve 104 also includes the inner surface 116 and the opening 120 that extends along a longitudinal axis of the sleeve, as previously described. The sleeve 104 further includes the peripheral surface 112, where in the present embodiment the peripheral surface 112 defines the first region 300 and the second region 320. In an additional embodiment, the peripheral surface 112 in the second region 320 defines a corrugated region 800.

In one embodiment, the corrugated region 800 has a pre-collapsed length 804. As the lead connector 140 is inserted into the connector block 806 (shown with a portion of the connector block removed) with the sleeve 104, the second end 110 of the sleeve 104 contacts the connector block 806. As the sleeve 104 is pushed to insert the lead connector 140 into the connector block 806, the corrugated region 800 begins to collapse until the corrugated region 800 has a collapsed length 810. In one embodiment, the difference between the pre-collapsed length 804 and the collapsed length 810 is equal to the desired length to be inserted into the pulse generator connector block 806. In the present embodiment, the lead connector 104 slides along the inner surface 116 of the sleeve in the second region 320 as the lead connector 104 is inserted into the connector block 806.

In an additional embodiment, the sleeve 104 further includes at least the first slit 124 to allow the body of the catheter lead 820 to pass through the sleeve 104, as previously described. Alternatively, the sleeve 104 further includes the second slit and a hinge, as previously described.

Figure 12:
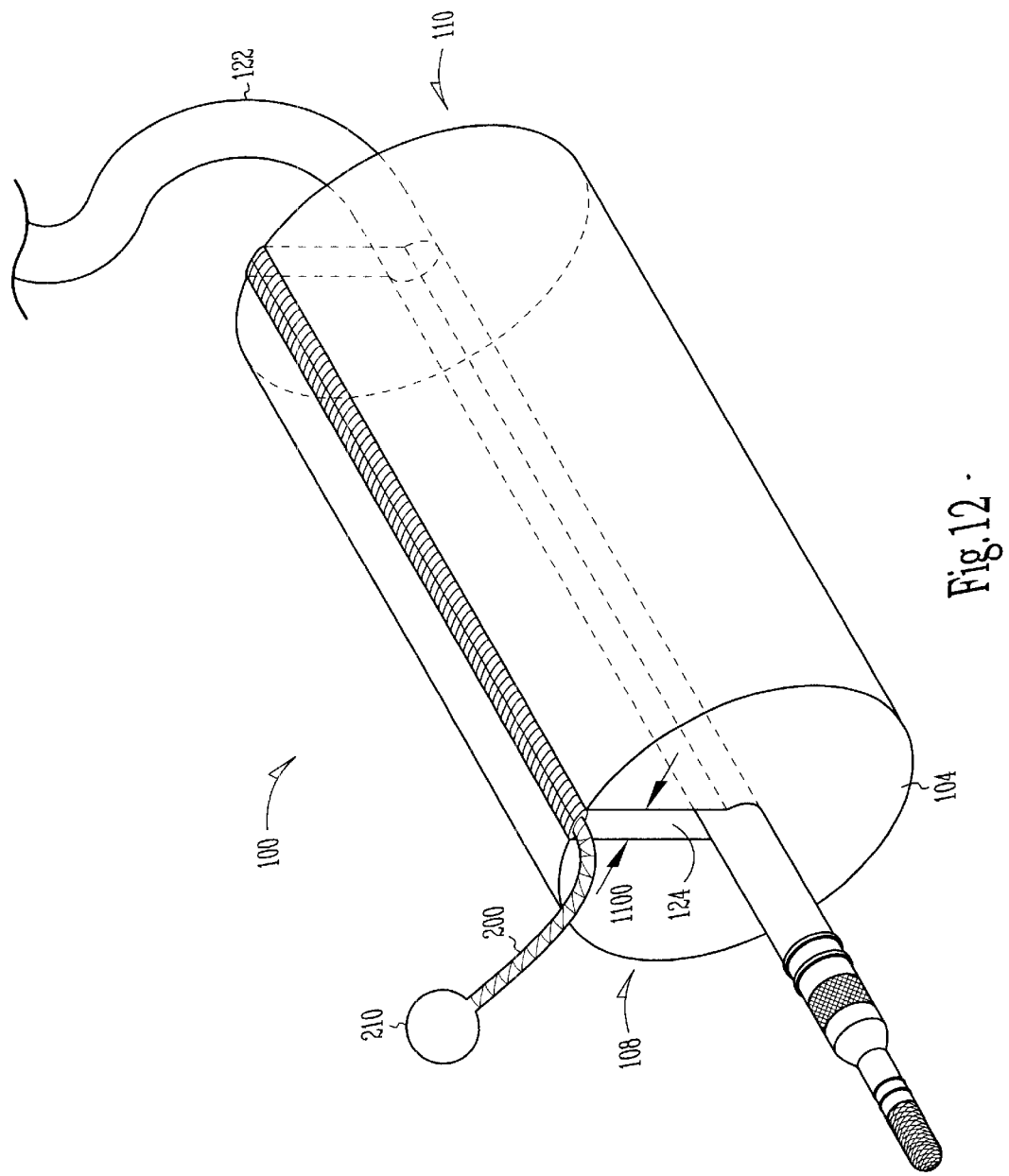
FIG. 12 is a schematic view of one embodiment of an apparatus according to the present subject matter.

Referring now to FIG. 12 there is shown an addition embodiment of the present subject matter. FIG. 12 shows an embodiment in which the first slit 124 is shown as having a predetermined distance 1100 between the first surface 262 and the second surface 264. Thus, the first slit 124 need not close completely, but enough to hold the body of the cardiac lead 122 in place while the lead is inserted into the implantable medical device. In one embodiment, the predetermined distance 1100 is determined by the type of material the sleeve 104 is constructed of relative to the diameter of the cardiac lead body. For example, when the sleeve 104 is constructed of silicone, the predetermined distance 1100 is from 75 percent to 25 percent of the cardiac lead 122 diameter. Alternatively, when the sleeve 104 is constructed of polyurethane, or blends of polyurethane, the predetermined distance 1100 is from 80 percent to 20 percent of the cardiac lead 122 diameter. Finally, when the sleeve 104 is constructed of a very rigid polymer, copolymer or polymer blend, the predetermined distance 1100 is from 99 percent to 1 percent of the cardiac lead 122 diameter.

In one embodiment, the apparatus of the present subject matter is applied and sterilized during the manufacturing process of the cardiac lead. In one embodiment, the exact size (e.g., length and diameter(s)) and shape of the sleeve 104 is determined by the dimensions of the cardiac lead and the manner in which the cardiac lead is inserted into the connector block of the implantable pulse generator.

We claim:

1. An apparatus, comprising:
    a sleeve having a peripheral surface, a first end and a second end, where the sleeve includes an opening extending from the first end to the second end and adapted to hold at least a portion of a cardiac lead, and where the sleeve includes a first slit extending from the peripheral surface to the opening and from the first end to the second end; and
    the cardiac lead includes a strain relief boot.

2. The apparatus of claim 1, including the cardiac lead, where at least a portion of the cardiac lead is positioned in the opening of the sleeve.

3. The apparatus of claim 2, where the cardiac lead has a proximal end and a lead connector at the proximal end of the cardiac lead, where the sleeve is distal to at least a portion of the lead connector.

4. The apparatus of claim 1, where the first slit opens to form a pass through opening in the sleeve which allows the cardiac lead to pass through the pass through opening.

5. The apparatus of claim 1, where the cardiac lead includes an outer diameter and the opening includes a first diameter, where the first diameter is smaller than the outer diameter of the cardiac lead.

6. The apparatus of claim 5, where the first diameter of the opening is approximately five (5) percent smaller than the outer diameter of the cardiac lead body.

7. The apparatus of claim 1, where the peripheral surface defines recessed portions of the sleeve that conform to portions of a hand.

8. The apparatus of claim 1, where the sleeve has a length between the first end and the second end from seven and one-half (7.5) centimeters to ten and one-half (10.5) centimeters.

9. An apparatus, comprising:
    a sleeve having a peripheral surface, a first end and a second end, where the sleeve includes an opening extending from the first end to the second end and adapted to hold at least a portion of a cardiac lead, and where the sleeve includes a first slit extending from the peripheral surface to the opening and from the first end to the second end;
    the cardiac lead includes an outer diameter and the opening includes a first diameter, where the first diameter is smaller than the outer diameter of the cardiac lead; and
    where the cardiac lead body includes a strain relief boot, and the opening includes a first region having the first diameter and a second region having a second diameter where the first diameter is less than the second diameter, and where the first region is adapted to hold at least a portion the cardiac lead and the second region is adapted to hold at least a portion of the strain relief boot.

10. An apparatus, comprising:
a sleeve having a peripheral surface, a first end and a second end, where the sleeve includes an opening extending from the first end to the second end and added to hold at least a portion of a cardiac lead, and where the sleeve includes a first slit extending from the peripheral surface to the opening and from the first end to the second end; and
a releasable closure strip which joins the sleeve along the first slit, where the releasable closure strip extends longitudinally between the first end and the second end of the sleeve.

11. The apparatus of claim 6, where the sleeve includes a second slit extending from the peripheral surface to the opening and from the first end to the second end to provide a first housing portion having a first inner surface, a first end and a second end, and a second housing portion having a first inner surface, a first end, and a second end, where the first inner surface of the first housing portion and the second housing portion are adapted to releasably hold the cardiac lead, and a hinge coupled to the first and second housing portions, where the hinge allows the first housing portion to move relative the second housing portion.

12. The apparatus of claim 11, where the peripheral surface defines a first region having a first outer diameter at the first end of the sleeve and a second region having a second outer diameter at the second end of the sleeve, where the first outer diameter is greater than the second outer diameter.

13. The apparatus of claim 2, where the hinge is adjacent the opening and the peripheral surface of the sleeve defines a region into which the sleeve moves as the sleeve is moved about the hinge.

14. The apparatus of claim 11, where the first housing portion and the second housing portion each include a longitudinal axis, and where the second exterior region of the first housing portion and the second housing portion is corrugated to allow the second region to collapse along the longitudinal axis of the first housing portion and the second housing portion.

15. The apparatus of claim 10, wherein the releasable closure strip is formed of material harder than the sleeve.

16. A method, comprising:
supporting at least a portion of a cardiac lead with a sleeve;
inserting the cardiac lead into an implantable pulse generator through the use of the sleeve;
removing a releasable strip from the sleeve; and
separating the sleeve from the cardiac lead.

17. The method of claim 16, where the lead includes a lead connector, and where supporting at least the portion of the lead includes positioning the sleeve distal the lead connector.

18. The method of claim 16, where supporting at least the portion of the lead includes at least partially encircling the cardiac lead with the sleeve.

19. The method of claim 16, where the implantable pulse generator includes a connector block and the sleeve includes a first end, and where inserting the cardiac lead includes positioning the sleeve on the cardiac lead so the first end of the sleeve abuts the connector block when the lead connector is seated in the connector block.

20. The method of claim 16, where the sleeve includes a slit, and where separating the sleeve from the cardiac lead includes passing the cardiac lead through the slit.

21. An apparatus, comprising:
a sleeve having a peripheral surface, a first end and a second end, where the sleeve includes an opening extending from the first end to the second end and adapted to hold at least a portion of a cardiac lead, and where the sleeve includes a first slit extending from the peripheral surface to the opening and from the first end to the second end; and
one or more expansion ribs associated with the sleeve.

22. An apparatus, comprising:
a sleeve having a peripheral surface, a first end and a second end, where the sleeve includes an opening extending from the first end to the second end and adapted to hold at least a portion of a cardiac lead, and where the sleeve includes a first slit extending from the peripheral surface to the opening and from the first end to the second end;
where the sleeve includes a corrugated region adapted to collapse as the lead is inserted in to the pulse generator.

23. The apparatus of claim 22, wherein the corrugated region has a pre-collapsed length and a collapsed length, where the difference between the pre-collapsed length and the collapsed length is equal to a predetermined length, and the predetermined length is the desired length the lead is to be inserted into the pulse generator.

* * * * *

UNITED STATES PATENT AND TRADEMARK OFFICE
CERTIFICATE OF CORRECTION

PATENT NO.   : 6,445,954 B1
DATED        : September 3, 2002
INVENTOR(S)  : Arthur L. Olive and Ronald W. Heil, Jr.

It is certified that error appears in the above-identified patent and that said Letters Patent is hereby corrected as shown below:

Column 13,
Line 5, delete "added" and insert -- adapted --, therefor.
Line 13, delete "claim 6" and insert -- claim 10 --, therefor.
Line 30, delete "claim 2" and insert -- claim 12 --, therefor.

Signed and Sealed this

Eleventh Day of February, 2003

JAMES E. ROGAN
*Director of the United States Patent and Trademark Office*